(12) United States Patent
Zarmanian et al.

(10) Patent No.: US 6,693,100 B1
(45) Date of Patent: Feb. 17, 2004

(54) PHARMACEUTICAL COMPOSITIONS FOR TREATING PSORIASIS

(76) Inventors: Iervant Zarmanian, Julius Meinl Gasse 15, A-1170 Vienna (AT); Jadranka Rogan-Grgas, Theresiengasse 30, A-1180 Vienna (AT)

( * ) Notice: Subject to any disclaimer, the term of this patent is extended or adjusted under 35 U.S.C. 154(b) by 0 days.

(21) Appl. No.: 10/070,687

(22) PCT Filed: Sep. 8, 2000

(86) PCT No.: PCT/EP00/08879

§ 371 (c)(1),
(2), (4) Date: Jun. 11, 2002

(87) PCT Pub. No.: WO01/19358

PCT Pub. Date: Mar. 22, 2001

(30) Foreign Application Priority Data

Sep. 10, 1999 (AT) .............................................. 1558/99

(51) Int. Cl.⁷ ............................................. A61K 31/497
(52) U.S. Cl. .............................. 514/252.11; 514/255.02
(58) Field of Search ........................ 514/252.11, 255.02

(56) References Cited

U.S. PATENT DOCUMENTS

| 3,941,790 A | 3/1976 | Creighton | .................... | 260/268 |
| 4,275,063 A | 6/1981 | Creighton | .............. | 514/252.11 |

FOREIGN PATENT DOCUMENTS

| EP | 0330381 | 8/1989 |
| WO | 9503054 | 2/1995 |

OTHER PUBLICATIONS

Curran, Charles F., et al., "Toxicity Profile of Dexrazoxane (Zinecard®, ICRF–187, ADR–529, NSC–169780), a Modulator of Doxorubicin Cardiotoxicity, " *Cancer Treatment Review*, 18:241–252, (1991).
Holcenberg, John S., et al., "Phase I Study of ICRF–187 in Pediatric Center Patients and Comparison of its Pharmacokinetics in Children and Adults," *Cancer Treatment Reports*, 70(6):703–709, (1986).
Schuler, D., et al., "Safety of Dexrazoxane in Children with all Undergoing Anthracycline Therapy: Preliminary Results of a Prospective Pilot Study," *Pediatr. Hematol. Oncol.*, 14(1):93–94 (1997).
Hochster, Howard S., "Clinical Pharmacology of Dexrazoxane," *Seminars in Oncology*, 25(4):37–42 (1998).
Hellmann, Kurt, "Overview Historical Development of Dexrazoxane," *Seminars in Oncology*, 25(4):48–54, (1998).
Carlson, Lisa, et al., "Pediatric Phase I Drug Tolerance: A Review and Comparison of Recent Adult and Pediatric Phase I Trials," *Journal of Pediatric Hematology/Oncology*, 18(3):250–256 (1966).
Vats, Tribhawan, et al., "Phase II Trial of ICRF–187 in Children with Solid Tumors and Acute Leukemia," *International New Drugs*, 9:333–337 (1991).

Blatt, Julie, "ICRF–187 as a Cardioprotectant in Children Treated with Anthracyclines," *Pediatric Hematology and Oncology*, 14(3):iii–vi, (1997).
Koeller, Jim M., et al., "Phase I Trial of ICRF–187 by 48–Hour Continuous Infusion," *Cancer Treatment Reports*, 65(5–6):459–463 (1981).
Liesmann, Jean, et al., "Phase I Evaluation of ICRF–187 (NSC–169780) in Patients with Advanced Malignancy," *Cancer*, 47:1959–1962 (1981).
Vogel, Charles L., et al., "Phase I Clinical Trial and Pharmacokinetics of Weekly ICRF–187 (NSC 169780) Infusion in Patients with Solid Tumors," *Investigational New Drugs*, 5:187–198 (1987).
Kolaric, Krsto, et al., Phase II Trial of Cardioprotection with Cardioxane (ICRF–187) in Patients with Advanced Breast Cancer Treated with 5–Fluorouracile, Doxorubicin and Cyclophosphamide (FAC), *Libri Oncology*, 22(2):101–106 (1993).
Venturini, Marco, et al., "Multicenter Randomized Controlled Clinical Trial to Evaluate Cardioprotection of Dexrazoxane Versus No Cardioprotection in Women Receiving Epirubicin Chemotherapy for Advanced Breast Cancer," *Journal of Clinical Oncology*, 14(12):3112–3120 (1996).
Wiseman, Lynda R., et al., "Dexrazoxane, A Review of its Use as a Cardioprotective Agent in Patients Receiving Anthracyline–Based Chemotherapy," *Drugs*, 56(3):385–403 (1998).
Wexler, L.H., et al., "ICRF–187 Reduces Doxorubicin–Induced Cardiotoxicity with no Impact on Response to Chemotherapy," Abstract Only, *Proceedings of ASCO*, vol. 12 (1993).
Rogan, J., "Cardioxane: Safety and Efficacy in Pediatric Patients; 3 Years Follow Up Report," *Intern. Symposium of Ped. Oncol.*, Prague (1998).
D. J. Atherton, R. S. Wells, M. R. Laurent, Y. F. Williams, *Razoxane (ICRF 159) in the Treatment of Psoriasis*, British Journal of Dermatology (1980) pp. 102, 307.
David J. Atherton, *Special Symposium on Dermatological Therapy: III Psoriasis and Mycosis Fungoides: Rzoxane*, Clinical and Experimental Dermatology (1981) 6 pp. 647–650.
de Jong EM, Ferrier CM, de Zwart A, Wauben–Penris PJ, Korstanje C, van de Kerkhof PC, *Effects of Tropical Treatment with Budesonide on Parameters for Epidermal Proliferation, Keratinization and Inflammation in Psoriasis*, J Dermatol Sci 1995 May; 9(3): 185–94.
B. B. Hasinoff, K. Hellmann, E. H. Herman, V. J. Ferrans, *Chemical Biological and Clinical Aspects of Dexrazoxane and Other Bisdioxopiperazines*, Current Medicinal Chemistry 1998, 5, 1–28.

(List continued on next page.)

Primary Examiner—Rebecca Cook
(74) Attorney, Agent, or Firm—Hunton & Williams LLP

(57) ABSTRACT

The use for the manufacture of a medicament for treating psoriasis of dexrazoxane, the d-isomer of 1,2-bis(3,5-dioxopiperazin-1-yl)-propane, or a physiologically acceptable salt thereof.

20 Claims, 1 Drawing Sheet

OTHER PUBLICATIONS

J. J. Horton and R. S. Wells, *Razoxane: A Review of 6 Years' Therapy in Psioriasis*, British Journal of Dermatology (1983) 109, 669–673.

P. J. Keen, *A Symposium in Psoriasis*, Pharmaceutical Medicine 1992; 6: 367–374.

Poster DS, Penta JS, Bruno S, Macdonald JS, *ICRF–187 in Clinical Oncology*, Cancer Clin Trials 1981; 4(2): 143–6.

Bonnekoh, B., et al., "Antiproliferative potential of zidovudine in human keratinocyte cultures," *J. Am. Acad. Dermatol.*, 25:483–90 (1991) (abstract).

Cihak, A., et al., "Azapyrimidine nucleosides: metabolism and inhibitory mechanisms," *Adv. Enzyme Regul.*, 24:335–54 (1985) (abstract).

De Haan, P., et al., "Effect of calcitriol on growth, differentiation, chemokine mRNA expression of cultured keratinocytes and on keratinocyte–T cell binding," *Acta Derm. Venereol. Suppl.* (Stockh), 186:52–4 (1994) (abstract).

Gorbsky, G.J., "Cell cycle progression and chromosome segregation in mammalian cells cultured in the presence of the topoisomerase II inhibitors ICRF–187 [(+)–1,2–bis(3, 5–dioxopiperazinyl–1–yl)propane; ADR 529] and ICRF–159 (Razoxane)," *Cancer Res.*, 54: 1042–8 (1994) (abstract).

Holcenberg, J.S., et al., "Phase I study of ICRF–187 in pediatric cancer patients and comparison of its pharmacokinetics in children and adults," *Cancer Treat. Rep.*, 70:703–9 (1986) (abstract).

Keshileva, Z.B., et al., "The combination of psoriasis with different types of lipoproteinemias 2. The characteristics of the dyslipoproteinemias caused by disorders in triacylglyceride transport in psoriasis," *Vestn. Dermatol. Venerol.*, 5:7–11 (1990) (abstract).

Koeller, J.M., et al., "Phase I trial of ICRF–187 by 48–hour continuous infusion," *Cancer Treat. Rep.*, 65:459–63 (1981) (abstract).

Liesmann, J., et al., "Phase I evaluation of ICRF–187 (NSC–169780) in patients with advanced malignancy," *Cancer*, 47:1959–62 (1981) (abstract).

Lowe, N.J., et al., "Animal assays for anti–psoriatic, retinoid and sun–protective agents," *Br. J. Dermatol.*, 111 Suppl 27:98–108 (1984) (abstract).

Muller, W., et al., "The treatment of psoriasis–arthritis with cyclosporin A, a new immunosuppressive agent," *Schweiz. Med. Wochenschr.*, 111(12): 408–13 (1981) (abstract).

Nickoloff, B.J., et al., "Additive and synergistic antiproliferative effects of cyclosporin A and gamma interferon on cultured human keratinocytes," *Am. J. Pathol.*, 131(1):12–8 (1988) (abstract).

Price, C.M., et al., "Sister chromatid exchange (SCE) frequency in lymphocytes of patients with colorectal carcinoma treated with razoxane," *Cancer Detect. Prev.*, 16(4):221–3 (1992) (abstract).

Priestley, G.C., "Proliferation and glycosaminoglycans secretion in fibroblasts from psoriatic skin: differential responses to retinoids," *Br. J. Dermatol.*, 117(5):575–83 (1987) (abstract).

Tanabe, K., et al., "Inhibition of topoisomerase II by antitumor agents bis(2,6–dioxopiperazine) derivatives," *Cancer Res.*, 51(18):4903–8 (1991) (abstract).

Vogel, C.L., et al. "Phase I clinical trial and pharmacokinetics of weekly ICRF–187 (NSC 169780) infusion in patients with solid tumors," *Invest. New Drugs*, 5(2):187–98 (1987) (abstract).

Von Hoff, D.D., et al., "Phase I study of ICRF–187 using a daily for 3 days schedule," *Cancer Treat. Rep.*, 65 (3–4):249–52 (1981) (abstract).

Von Hoff, Daniel D, "Phase I trials of Dexrazoxane and Other Potential Applications for the Agent," *Seminars in Oncology*, vol. 25:31–35, (1998) (4/10).

Witiak, D.T., et al., "Dioxopiperazines: Chemistry and Biology," *Progress in Drug Research*, 35:249–363 (1990).

Atherton, D., et al., "Razoxane (ICRF 159) in treatment of psoriasis", British Journal of Dermatology, vol. 102, No. 3, 307–317, (1980).

Atherton, D., et al., "Razoxane (ICRF 159) in psoriasis", Lancet vol. 2, 1296, (1976).

Mom, A., et al. "Razoxane in the treatment of psoriatic patients resistant to or intolerant of PUVA, methotrexate and etretinate", Acta Dermato–Venereologica, vol. 62, No. 4, 357–358, (1982).

Horton, J., et al., "Long–term razoxane therapy of psoriasis", British Journal of Dermatology, vol. 109, 26, (1983).

PHARMACEUTICAL COMPOSITIONS FOR TREATING PSORIASIS

This claims benefit of U.S. Ser. No. 60/183,806 filed Feb. 22, 2000.

FIELD OF INVENTION

This invention relates to pharmaceutical compositions based on 1,2-bis(3,5-dioxopiperazin-1-yl)-propane and pharmaceutically acceptable salts thereof.

1,2-bis(3,5-dioxopiperazin-1-yl)-propane is of formula

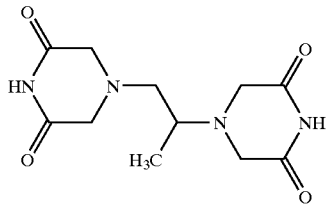

and it may exist in the d-isomeric form, the 1-isomeric form and in the racemic d1-form.

BACKGROUND OF THE INVENTION

The racemic d1-form of 1,2-bis(3,5-dioxopiperazin-1-yl)-propane is known as razoxane. Compounds of this kind belong to the family of bis-dioxopiperazines, which have been known for a long time, particularly as anti-tumor agents. This class of compounds, their use and preparation are described in, e.g. GB-A-1 234 935, GB-A-1 374 979, U.S. Pat. No. 4,275,063, EP-A1 491 053, EP-A1 256 137, EP-A1 230 474, EP-A2 014 327 and EP-A1 125 475.

The bis-dioxopiperazines represent lipophilic derivatives of EDTA (ethylene diamino tetraacetic acid), a substance known as a chelating agent. As such they are thought to act by chelating iron, thereby reducing site-specific oxygen radical production. The bis-dioxopiperazines exert topoisomerase II inhibitory activity which presumably is responsible for the antitumor activity of these drugs. The d-enantiomer of razoxane is known as dexrazoxane. The current clinical use of dexrazoxane is to prevent doxorubicin-induced cardiac disease in patients with metastatic breast cancer.

Dexrazoxane is commercially available as the hydrochloride salt. In Europe, dexrazoxane.HCl is available from Chiron, Inc under the registered trade mark Cardioxane, whilst in the US it is available from Pharmacia Upjohn under the registered trade mark Zinecard. A discussion of the chemical, biological and clinical aspects of dexrazoxane and other bis-dioxopiperazines can be found in Current Medicinal Chemistry (1998) 5, 1–28. GB-A-1 234 935 is one of the oldest publications on bis-dioxopiperazines and describes their preparation through cyclisation of the corresponding tetracarboxamidomethyl derivatives through heating together with polyphosphoric acid. The therapeutic spectrum of these drugs includes certain forms of cancer, including leukaemia, and certain non-malignant forms of proliferative disease.

For the preparation of dexrazoxane mainly two methods have been described (U.S. Pat. No. 3,941,790). In the first method 1,2-diaminopropane tetraacetic acid and formamide are heated together to yield the cyclic product. In the second method the corresponding tetraamide of the above tetraacid is heated in polyphosphoric acid or phenol, also leading to cyclisation of the compound (see the previously mentioned GB-A-1 234 935).

Other methods for preparation of dexrazoxane are known, e.g. described in U.S. Pat. No. 4,764,614 or EP-A-0 330 381.

The preparation of a lyophilised composition containing dexrazoxane that is stable and less light-sensitive is described in detail in U.S. Pat. No. 5,760,039.

Psoriasis is a chronic skin disease characterised by scaling and inflammation. The cause of psoriasis is unknown but recent research indicates that it is likely to be an autoimmune disease. Psoriasis is a serious and unpleasant condition which has no cure and not all treatments work for each individual.

Psoriasis can be very painful, but the pain is more than skin deep. The emotions suffer as well. It presents people with physical limitations, disfiguration, and its tedious daily care always demands too much time. Embarrassment, frustration, fear and depression are common. In extreme cases, a loss of self-esteem results in a complete withdrawal from society. Various kinds of temporary relief are available and they work with varying degrees of success. Treatments and medications are often time consuming and expensive but one thing is certain: the symptoms may come and go, but they almost always come again. It is a lifelong disease.

Psoriasis is treated using what is sometimes called the "1-2-3" approach. Step 1 is topical treatment, step 2 is phototherapy and step 3 is systemic treatment. Medicines currently prescribed for systemic treatment are the immunosuppressants methotrexate and cyclosporine A, hydroxyurea and retinoids.

Methotrexate and cyclosporine A have unpleasant and potentially dangerous side effects. Moreover, all these treatments leave patients with recurrent psoriasis and because different patients respond differently to varying treatments, it would be very welcome to have additional weapons in the therapeutic armoury.

In 1976, D. J. Atherton (Lancet, ii, 1296, 1976) for the first time proposed the use of racemic razoxane (ICRF-159) for the treatment of psoriasis. A review on the therapeutic use of razoxane in psoriasis can be found in the British Journal of Dermatology (1980) 102, 307. The drug had relatively good efficacy and good tolerability, but some unpleasant side effects and certain toxicities were noticed. Therefore administration of the drug was recommended only under strictly controlled conditions. Horton and Wells (British Journal of Dermatology (1983) 109, 669–673) again reported the relatively good success of treatment with razoxane, however, a considerable proportion of patients stopped treatment because of relatively severe side effects. The most frequently seen side effect was neutropenia, a potentially fatal depletion of neutrophiles (a subset of leukocytes), which was reported to occur in a number of patients even on low doses insufficient to control psoriasis. Other side effects were alopecia, nausea, diarrhoea, nasal bleeding, leg ulceration, lethargy, headaches and squamous epitheliomata.

Because of this and further complications arising after chronic administration, razoxane was not developed further and today is not recommended for treatment of psoriasis. Hitherto, therefore, the known facts about razoxane have been that it cannot be used both safely and effectively to treat psoriasis.

SUMMARY OF THE INVENTION

Surprisingly, it has now been demonstrated that the d-enantiomer of 1,2-bis(3,5-dioxopiperazin-1-yl)-propane, dexrazoxane, by itself can be used to treat psoriasis safely and effectively. Indeed, our studies indicate that the treatment results are truly remarkable for some patients, with relief from refractory psoriasis for periods of up to at least one year. No serious side effects have been reported in clinical trials to date, with the vast majority of patients being free of neutropenia and no recorded cases of vomiting, nausea or diarrhoea.

DETAILED DESCRIPTION OF THE INVENTION

According to the present invention a new pharmaceutical composition for treatment of psoriasis contains as active compound dexrazoxane, or a pharmaceutically acceptable salt thereof, together with a pharmaceutically acceptable carrier and/or excipient.

The invention also includes a method of treating psoriasis in a patient, comprising administering to the patient a therapeutically effective amount of dexrazoxane, the d-isomer of 1,2-bis(3,5-dioxopiperazin-1-yl)-propane, a compound of formula

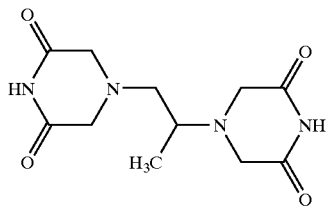

or a physiologically acceptable salt thereof.

BRIEF DESCRIPTION OF THE DRAWING

The invention is further described below with reference to accompanying FIG. 1, which is a graphical presentation of the mean value (n=7) of the Psoriasis Area and Severity Index (PASI) over a treatment protocol having three dexrazoxane administration cycles.

The method may comprise administering the dexrazoxane by injection or infusion (or by other internal administration route, for example oral) at a daily dosage of, for example, between 250 mg and 1750 mg, and in one suitable protocol comprises administering the dexrazoxane at increasing dosages, for example at a first daily dosage for an initial period of up to e.g. 5 days, a second daily dosage for a second period of up to e.g. 5 days and a third daily dosage for a third period of up to e.g. five days. The initial, second and third periods may be spaced apart and preferably are one or two days long; one of the initial, second and third periods is dispensed with in some treatment protocols. For an adult, the first daily dosage is usually from about 250 mg to about 750 mg (e.g. about 500 mg), the second daily dosage is usually from about 750 mg to 1250 mg (e.g. about 1000 mg), and the third daily dosage is usually from about 1250 mg to 1750 mg (e.g. about 1500 mg).

Figure 1:
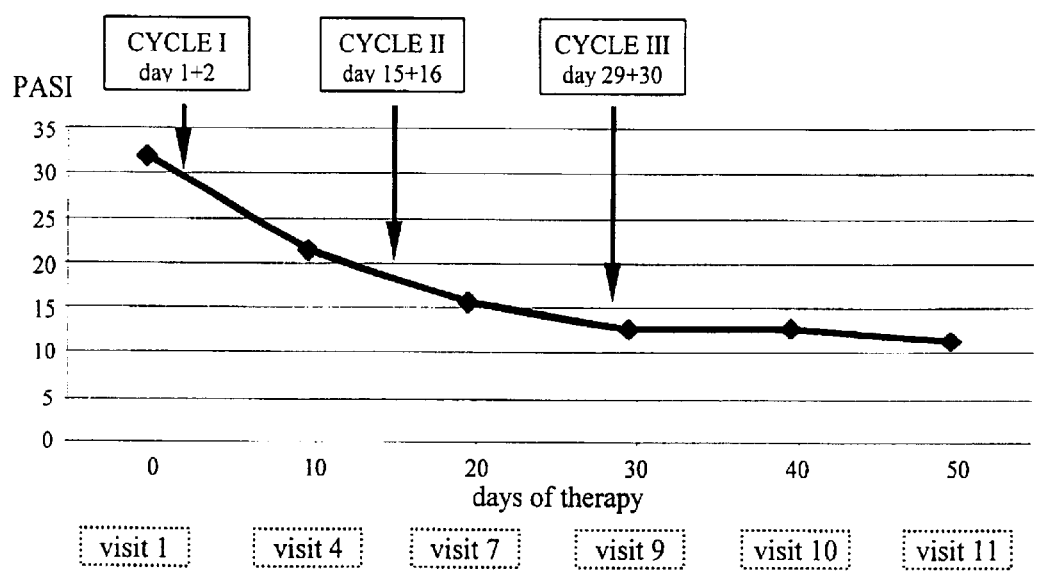

In any event, the most preferred protocols for internally, e.g. parenterally, administering dexrazoxane involve administering the dexrazoxane at intervals, for example with an interval between administration periods of from 5 to 20 days, more usually from 8 to 16 days and most preferably of from 10 to 14 days, e.g. 12 days. As already indicated, an administration period may last two successive days, on each of which dexrazoxane is administered. Alternatively single day administration periods may be used, or administration periods of more than two days, in which case dexrazoxane may be administered on all of the days or only some of them. Particularly preferred protocols consist of three spaced administration periods, for example of two days in length and/or separated by intervals of 12 days; thus a protocol may consist of the three cycles appearing in FIG. 1. The administration protocol may be repeated as necessary, for example after a period of between a month and a year or more. The parenteral administration is suitably by infusion or injection and the dexrazoxane is usually (but not exclusively) administered in the form of a salt.

The dosage may be varied, for example increased, over the course of the treatment. In particular, the dosage may be increased after the first administration period of the protocol described in the previous paragraph if the patient's initial response is not adequate. Conveniently, an adult is administered a dose of from about 250 mg to about 750 mg on each day of an initial two day administration period, after which the dose may be maintained or increased (e.g. to about 750 mg to about 1250 mg). After the second administration period, the dosage may be maintained or, if necessary increased (or even decreased) for the third administration period. The dosage is conveniently, but not necessarily, altered in steps of 500 mg.

The dexrazoxane weights and weight percentages specified in this application refer to dexrazoxane hydrochloride, i.e. they relate to dexrazoxane as the hydrochloride salt. If an alternative form is used appropriate adjustments should be made on the basis of the relative molecular weights of the two forms. Similarly, dosages must be suitably adjusted for the treatment of children.

In one class of methods, therefore, the dexrazoxane is administered intravenously or otherwise by injection or infusion. In current practice, the solutions for injection or infusion are made by reconstituting lyophilised dexrazoxane just prior to administration. The lyophilisate may be packaged in an amount corresponding to the unit dosage to be used and packages containing about 250 mg, from about 750 mg to about 1250 mg or about 1250 mg to about 1750 mg are each included in the invention. The invention also includes the use of dexrazoxane to manufacture liquid dexrazoxane preparations in ready to use form, and the administration of such ready to use liquid formulations (solutions).

In another class of methods the dexrazoxane is administered topically, transdermally or percutaneously, e.g. in the form of an ointment, lotion or plaster. Other methods comprise the oral administration of the dexrazoxane, for example in tablet form. The dexrazoxane may be administered in the form of a suppository. Alternatively the dexrazoxane is administered as a topical formulation, for example as an ointment, cream or gel. The concentration of dexrazoxane is not critical. However, some topical formulations contain at least 0.1 wt % dexrazoxane, and more usually contain from 0.25 wt % and especially 0.5 wt % to 5 wt % or more dexrazoxane. One class of formulations contains 1–2 wt % of dexrazoxane. The invention includes formulations adapted for topical administration to the exclusion of oral or parenteral administration or administration by injection or infusion. The topical formulations are suitably packaged in tubes of up to 100 g, associated with instructions to use them to treat psoriasis.

The topical formulations may by way of example contain conventional carriers. By way of non-limiting example, the ointments may contain water and one or more hydrophobic carriers selected from liquid paraffin, polyoxyethylene alkyl ether, propylene glycol and white vaseline. The carrier compositions of the creams are typically based on water and white vaseline, in combination with glycerol and more minor components, e.g. one or more of glycerinemonostearate, PEG-glycerinemonostearate and cetylstearyl alcohol. The gels may by way of example be formulated using isopropyl alcohol and water, suitably in combination with minor components, for example one or more of glycerol and hydroxyethyl cellulose.

The dexrazoxane may be used in combination therapy, for example with a non-steroidal anti-inflammatory drug, a TNF inhibitor or a vitamin. The invention therefore includes products, especially comprising a topical formulation, containing dexrazoxane and an agent useful for treating psoriasis or relieving its symptoms as a combined preparation for simultaneous, separate or sequential use in treating psoriasis. The product may be a topical formulation containing the two or more active agents in combination.

During a clinical trial a rapid amelioration of disease-associated signs was seen even in particularly resistant cases that had a long history of psoriasis. The itch diminished several hours after the first administration and it practically disappeared after the next dose. The scaling was reduced, the madescence disappeared, the thickness of the affected area was significantly reduced and the patients were free of arthralgia.

The patients showed marked subjective and objective responses as a 25–30% regression of the skin lesions, without experiencing the known side effects of razoxane.

The preferred formulation is a sterile solution for injection or infusion, but ointments, lotions, oral forms, plasters and suppositories may also be employed.

EXAMPLES

The invention is illustrated in the following examples:

Clinical trials to demonstrate the efficacy of dexrazoxane:

Example 1

This patient, a 55 year old male, had a 20 year history of psoriasis. The disease started after mental stress (loss of near person) with a rash on the hairy part of the head. From the very onset of the disease the patient received intensive treatment with vitamins $B_{12}$, $B_6$, $B_2$, and calcium. He had artificial hyperthermia with pyrogenal injections, methotrexate, various ointments (e.g. salicylic ointment) under a dermatologist's observation at a specialised clinic. In spite of the treatment the psoriatic rash was spreading over the trunk, upper and lower extremities and it was accompanied by a marked general itch. The patient had practically no remissions. Concurrent diseases were grade II hypertension and chronic cholecystopancreatitis.

At the first examination the patient complained about itching all over the body (resulting in insomnia) and pain in the large joints (mainly knees). The skin on the back, buttocks, chest and arms was covered with a erythematous papular and pustular rash with a white coating (desquamation). A similar though less intense rash was seen on the legs. The patient's general status, the haematological and biochemical profiles were within normal.

On the first and the second day of the treatment cycle the patient received the first doses of Cardioxane® (dexrazoxane.HCl) at 500 mg each day by intravenous drip infusion. On day 15 the patient reported of the amelioration of itch several hours after the first Cardioxane® administration. The itch practically disappeared after the next dose of Cardioxane® therapy at 1000 mg on day 16. The patient presented with amelioration of scaling, disappearance of madescence, amelioration of hypernia and flattening of rash, and complete disappearance of anthralgia. The patient slept well for the first time in a long disease period. The effect was still preserved at the examination on day 29 and day 30 when the patient was given the last two injections of Cardioxane® at 1500 mg each.

At the last examination on day 29 the patient presented with flattening of the rash, disappearance of some lesions and appearance of normal skin areas (up to 2 cm in diameter, especially on the lower limbs). A total reduction by 25%–30% of total skin lesions was diagnosed. The itch, although returning briefly approx. 1.5 weeks after the first two injections, did not re-appear after the 3rd and 4th injections, nor did arthralgia. There were no adverse events after any of the injections.

Example 2

This patient, a 50 year old male, had suffered from generalised psoriasis for 25 years. The rash first appeared on the head and the right upper limb to spread over the trunk and upper limbs later. The patient had received therapies similar to the patient described in Example 1. In addition he received UV therapy, peloids, sulfurated hydrogen baths, but without lasting effect. The patient had no concurrent illness except asthenia, sinus arrhythmia and left ventricular hypertrophy. The skin on the back, lumbar region and shoulders was covered with merged erythematous papular, bullar and desquamating lesions. The rash on the lateral chest walls and on the lower limbs was mainly erythematous and less marked. The skin lesions covered about 50% of the body surface. The patient did not complain of itch.

The patient was given 6 intravenous drip injections with Cardioxane® according to the following schedule:

On day 1 and day 2 each 500 mg Cardioxane®, on day 15 and day 16 each 1000 mg Cardioxane®, and on day 29 and day 30 each 1500 mg Cardioxane®.

At examination on day 15 and day 29 the patient presented with a mild amelioration of erythema on the back. The remaining lesions demonstrated no change. There were no side effects.

Example 3

This patient, a 37 year old female, had a 16 year history of the disease, manifesting itself after an abortion and mental stress. The psoriatic rash appeared on the hairy part of the head and neck to spread further over the body. The patient received insolation with but a temporary effect. The patient had had 4 hospitalisations to receive therapy with vitamins, calcium, and various ointments. After a period of intense stress due to the loss of a close person the patient had a sharp exacerbation of the disease, with erythematous lesions covering most of the body. The patient also had a history of periodic episodes of allergic asthmatic bronchitis.

At the first examination on day 1 the patient presented with continuous erythematous papular psoriatic rash with desquamation on the front abdominal wall (below the submammal fold), the inguioileac, the lumbosacral, the gluteal regions and the lower limbs, severe itch, and scraping tubular breathing (asthmatic bronchitis). Of note was also a marked increase in the eosinophile count.

The patient received 6 intravenous drip injections of Cardioxane® according to the protocol given in Example 2. At examination on day 15 the patient reported the complete disappearance of skin itch at 2 or 3 days after the first injection of Cardioxane®. The lower half of the abdomen as well as the upper gluteal quadrants were practically free of rash. There were no adverse events after the injections of Cardioxane®, except a mild pain along the vein path at the injection site.

At the examination on day 30 the patient presented with complete regression of about 80% of the rash, with residual depigmentation in the lumbosacral region and on the legs. The itch was still absent. No adverse events were reported, despite the concurrent allergic status of the patient.

Example 4

The efficacy and tolerability of dexrazoxane in patients with refractory psoriasis was assessed in a clinical study.

After screening, eligible patients received 500 mg of Cardioxane® by intravenous infusion on each of two consecutive days. They were reviewed 7 and 14 days after the first day of treatment. The patients received the second cycle of treatment, which consisted of either 500 mg Cardioxane® by intravenous infusion, on each of two consecutive days (days 15 and 16, in this case), if a complete response had occurred, or 1000 mg Cardioxane® by intravenous infusion, on each of two consecutive days (days 15 and 16, in this case), if an incomplete response had occurred.

A third cycle of treatment was given after the same interval (days 29 and 30, in this case). Patients who showed a complete response received the same dose as they received in the second cycle, whilst one patient, who showed no response, received two doses of 1500 mg.

The primary efficacy parameter was the percentage reduction in skin area and severity affected by psoriasis, as determined by the standardised assessment of the Psoriasis Area and Severity Index (PASI).

Seven patients have been enrolled in the study and all patients have completed a follow-up period of two weeks. At the beginning of the treatment, the PASI-scores ranged between 23.1 and 44.1, with a mean score of 31.9. Most of the patients did respond to the treatment, except for one patient, who was absolutely resistant to therapy. At the end of the third treatment cycle, the PASI-scores ranged between 3.4 and 29.7, with a mean score of 11.4.

At 11 weeks after the start of the therapy, the mean reduction in PAST was 65%, with a maximum reduction of 88%, and one resistant case. The tolerability of the treatment was excellent, and no serious adverse events were reported. In addition, the therapy with Cardioxane® resulted in better and faster relief of symptoms associated with psoriatic arthritis, when compared to treatment with cyclosporine A (which is the standard treatment in this indication and had been used previously in the clinic).

The results are shown in Table 1 and represented graphically in FIG. 1.

TABLE 1

The effect of Cardioxane ® treatment on the Psoriasis Area and Severity Index (PASI)

| visit No | PASI score and patient number/initial | | | | | | |
|---|---|---|---|---|---|---|---|
| | 1/HH | 2/MR | 3/MZ | 4/PH | 5/PZ | 6/FJ | 7/DJ |
| v1 | 23.1 | 43.6 | 29.8 | 27.0 | 29.1 | 44.1 | 26.6 |
| v4 | 11.3 | 36.3 | 18.4 | 18.6 | 16.9 | 24.8 | 23.6 |
| v7 | 7.7 | 23.1 | 11.6 | 13.5 | 9.9 | 20.3 | 23.0 |
| v9 | 6.5 | 15.6 | 9.7 | 10.8 | 9.3 | 15.6 | 21.8 |
| v10 | 6.5 | 12.3 | 7.1 | 12.0 | 7.8 | 15.6 | 28.5 |
| v11 | 5.6 | 14.0 | 6.5 | 5.2 | 3.4 | 15.3 | 29.7 | mean PASI score at the start of treatment (n = 7): $\bar{x}$ = 31.9
mean PASI score after 7 weeks (n = 7); $\bar{x}$ = 11.4
mean reduction in PASI score (n = 7); 65%

Of 7 patients treated, only one was diagnosed with mild, reversible leukopenia (approximately 3×10E9 cells per liter, it was classified as grade I toxicity according to World Health Organisation criteria) after the first week of treatment. This neutropenia disappeared after another week, and the counts were normal from then on. All other patients had normal white blood cell counts. The assessment of toxicity was according to the WHO criteria: grade 0 (non-toxic, a count of more than 4×10E9 leukocytes per liter), grade 1 (mild) to grade 4 (most severe). No cases of vomiting, nausea, or diarrhoea were recorded.

The most up to date information is that most of the patients are still in remission one month after the last injection. Three patients were not cleared entirely, but the disease is in such mild manifestation that it can be well treated with conventional remedies, such as ointments. All these patients previously suffered greatly from their psoriasis which was refractory to other treatments.

In a separate study, which has been in progress for a longer period, of three patients with refractory psoriasis, one patient is still relatively free of lesions and symptoms after one year. This patient, who previously suffered distressing refractory psoriasis, can be treated with conventional emollients. Dexrazoxane therefore has the potential to provide remarkable long term relief from refractory psoriasis and a low level of side effects.

Example 5

A solution for infusion is prepared:

Cardioxane® is available in 36 ml brown glass vials. Each vial contains 500 mg lyophilised active substance, the hydrochloric acid salt of dexrazoxane. For reconstitution the contents of each vial is dissolved in 25 ml sterile water for injection. The contents will dissolve within a few minutes under gentle agitation. The pH of the resulting solution is approx. pH 1.6.

For infusion the solution needs to be further diluted. Preferred are sodium lactate UP (0.16M) or Ringer-Lactate BP for infusion. Both solutions give an infusion fluid with an acceptable pH.

Dilution of 4 vials of Cardioxane ® (reconstituted)

| Solution | Volume (ml) | pH | Total volume after dilution (ml) |
|---|---|---|---|
| Sodium lactate UP (0.16 M) | 500 | 4.66 | 600 |
| | 300 | 4.47 | 400 |
| | 100 | 3.80 | 200 |

-continued

Dilution of 4 vials of Cardioxane ® (reconstituted)

| Solution | Volume (ml) | pH | Total volume after dilution (ml) |
|---|---|---|---|
| Ringer-Lactate BP | 500 | 3.45 | 600 |
|  | 400 | 3.19 | 500 |
|  | 300 | 2.85 | 400 |
|  | 100 | 2.14 | 200 |

Example 6

Tablets of the following composition are prepared:

|  | mg/tablet |
|---|---|
| Cardioxane ® | 100 mg |
| Avicel ® (microcrystalline cellulose) | 16 mg |
| starch | 9 mg |
| hydroxypropylmethyl cellulose | 3 mg |
| magnesium stearate | 1 mg |
| polyvinylpyrrolidone | 0.6 mg |
| colloidal silicon dioxide | 0.3 mg |

Half the total quantity of hydroxypropylmethyl cellulose, polyvinylpyrrolidone and a sufficient amount of water are mixed together and stirred until dissolved (binder solution). Cardioxane®, starch, and the rest of the hydroxypropylmethyl cellulose are mixed in a granulator and stirred for 10 minutes. The granulation process is started by spraying the binder solution. After spraying and blending the product is dried in the same apparatus and discharged when the water content is below 2.8–3.0%. The granulate is passed through an oscillating granulator equipped with a 1.2 mm stainless steel screen. The granulate is mixed with starch, microcrystalline cellulose, and colloidal silicon dioxide for 20 minutes under rotation. The magnesium stearate is added and blended with the granulate. The final product is compressed at 130 mg on a rotary tableting unit equipped with 10 mm diameter lenticular punches.

Example 7

An ointment of the following composition is prepared:

|  | g/100 g ointment |
|---|---|
| Cardioxane ® | 1.5 g |
| liquid paraffin | 10 g |
| polyoxyethylene-20-stearylether | 15 g |
| propyleneglycol | 5 g |
| white vaseline | 40 g |
| purified water | 28.5 g |

Cardioxane® is reconstituted in cold water. The other ingredients are melted at 60° C. and stirred. Cardioxane® is added and the product is stirred until cold.

Example 8

A cream of the following composition is prepared:

|  | g/100 g cream |
|---|---|
| Cardioxane ® | 1 g |
| glycerinemonostearate (Tegin M ®) | 4 g |
| PEG-20-glycerinmonostearate (Tagat S2 ®) | 7 g |
| cetylstearyl-alcohol | 6 g |
| viscous paraffin | 7.5 g |
| white vaseline | 25 g |
| glycerol 85% | 10 g |
| magnesium sulfate heptahydrate | 0.5 g |
| purified water | 39 g |

The glycerinemonostearate, PEG-20-glycerinemonostearate, cetylstearyl-alcohol, paraffin and vaseline are heated to 60° C. and stirred. The smaller part of the water is briefly boiled and cooled to 60° C., the magnesium sulfate and glycerol are added and stirred. Cardioxane® is reconstituted in the other part of the water and added to the solution. Now the two phases are emulsified in an emulsifier, and after cooling a homogeneous creme is obtained.

Example 9

A gel of the following composition is prepared:

|  | g/100 g gel |
|---|---|
| Cardioxane ® | 1.2 g |
| isopropyl alcohol | 20 g |
| glycerol 100 % | 2 g |
| hydroxyethyl cellulose | 1.8 g |
| purified water | 75 g |

Half of the total quantity of water, and glycerol are heated to 50° C.; hydroxyethyl cellulose is added and stirred until a homogeneous gel is obtained. Cardioxane® is reconstituted with the rest of the water and added under constant stirring. The gel is cooled to 25° C., the isopropyl alcohol is added and the mixture is stirred under vacuum until a homogeneous gel is obtained.

What is claimed is:

1. A method of treating psoriasis in a patient, comprising administering to the patient a therapeutically effective amount of dexrazoxane, which is the d-isomer of 1,2-bis(3,5-dioxopiperazin-1-yl)-propane, or a physiologically acceptable salt thereof.

2. The method according to claim 1, wherein the dexrazoxane is administered together with a physiologically acceptable diluent, carrier or excipient.

3. The method according to claim 2, wherein the physiologically acceptable salt is dexrazoxane HCl.

4. The method according to claim 2, wherein the dexrazoxane is administered by injection or infusion.

5. The method according to claim 2, wherein the dexrazoxane is administered topically, transdermally, or percutaneously.

6. The method according to claim 5, wherein the dexrazoxane is in the form of an ointment, lotion, or plaster.

7. The method according to claim 2, wherein the dexrazoxane is administered orally.

8. The method according to claim 2, wherein the dexrazoxane is in the form of a suppository.

9. The method according to claim 2, wherein the patient is an adult and the method comprises the step of administering the dexrazoxane by infusion or injection in a dosage of between about 250 mg to about 750 mg calculated as dexrazoxane hydrochloride.

10. The method according to claim 2, wherein the patient is an adult and the method comprises the step of administering the dexrazoxane by infusion or injection in a dosage of between about 750 mg to about 1250 mg calculated as dexrazoxane hydrochloride.

11. The method according to claim 2, wherein the patient is an adult and the method comprises the step of administering the dexrazoxane by infusion or injection in a dosage of between about 1250 mg to about 1750 mg calculated as dexrazoxane hydrochloride.

12. The method according to claim 2, wherein the patient is an adult and the method comprises the steps of:

(a) administering the dexrazoxane by infusion or injection in a dosage of between about 250 mg to about 750 mg calculated as dexrazoxane hydrochloride;

(b) on a subsequent day administering the dexrazoxane by infusion or injection in a dosage between about 750 mg to about 1250 mg calculated as dexrazoxane hydrochloride; and (c) on a subsequent day administering the dexrazoxane by infusion or injection in a dosage between about 1250 mg to about 1750 mg calculated as dexrazoxane hydrochloride.

13. The method according to claim 2, wherein the dexrazoxane is administered topically.

14. The method according to claim 13 wherein the dexrazoxane is administered as a topical formulation containing from about 1 wt % to about 2 wt % dexrazoxane calculated as dexrazoxane hydrochloride.

15. The method according to claim 4, wherein there is administered to the patient a physiologically acceptable salt of dexrazoxane.

16. The method according to claim 15, wherein the physiologically acceptable salt of dexrazoxane is dexrazoxane HCl.

17. The method according to claim 5, wherein there is administered to the patient a physiologically acceptable salt of dexrazoxane.

18. The method according to claim 17, wherein the physiologically acceptable salt of dexrazoxane is dexrazoxane HCl.

19. The method according to claim 12, wherein there is administered to the patient a physiologically acceptable salt of dexrazoxane.

20. The method according to claim 12, wherein the physiologically acceptable salt of dexrazoxane is dexrazoxane HCl.

* * * * *